United States Patent [19]

Whattam

[11] 4,132,225
[45] Jan. 2, 1979

[54] MICRO BLOOD COLLECTOR

[75] Inventor: George F. Whattam, Timonium, Md.

[73] Assignee: Hynson, Westcott & Dunning, Inc., Baltimore, Md.

[21] Appl. No.: 742,744

[22] Filed: Nov. 18, 1976

[51] Int. Cl.$^2$ ............................................. A61B 10/00
[52] U.S. Cl. .................................. 128/2 F; 215/306; 220/375
[58] Field of Search ................ 128/DIG. 5, 2 G, 2 F, 128/276; 220/339, 375, 38.5; 215/306; 23/259, 292; 73/425.2, 425.4 R, 425.4 P, 425.6; 222/541, 542

[56] References Cited

U.S. PATENT DOCUMENTS

| 1,924,242 | 8/1933 | Kaye | 215/306 |
| 2,655,152 | 10/1953 | Turner et al. | 128/DIG. 5 |
| 3,282,478 | 11/1966 | Russell | 222/542 |
| 3,518,164 | 6/1970 | Andelin et al. | 128/2 F |

FOREIGN PATENT DOCUMENTS 1424943  2/1965  France ................................. 215/306

Primary Examiner—Dalton L. Truluck
Assistant Examiner—V. Millin
Attorney, Agent, or Firm—Burns, Doane, Swecker & Mathis

[57] ABSTRACT

The blood collector of the present invention is a one-piece molded container consisting of three basic components - a) a base, b) a top, and c) a cap, with connecting straps. The top of the device is lockable to the base by male and female interlocking snap-fit rings, to prevent the top of the collector from "popping" off the base when squeezing the collector to produce suction for the withdrawal of blood from an animal. The tethered cap produces a self-contained unit for transporting blood collected in the field to a laboratory for centrifuging and testing. After centrifuging, by removing the top from the base there is easy accessibility to the plasma or serum.

2 Claims, 6 Drawing Figures

MICRO BLOOD COLLECTOR

The present invention relates to the container art, and is concerned with the provision of an improved blood collector which in combination with a standard hypodermic needle constitutes a complete blood-drawing (or, "bleeding") device.

Blood collectors comprising a container and a cooperating closure — whether or not of the "captive" sort — are broadly "old" in this art, having been described in a plurality of disclosures including U.S. Pat. No. 2,958,439, Yochem and U.S. Pat. No. 3,419,179, Deuschle et al, as illustrative examples. Such articles were not adapted for use in drawing a sample of fluid (e.g. blood) from an animal but rather were adapted merely to receive and store a sample after the latter had been drawn by a separate device.

A blood collector which was adapted for use in drawing a sample and for receiving and storing such sample when drawn had been proposed in U.S. Pat. No. 3,288,318, Corbin et al. Such a collector was not of a unitary nature, being assembled from two or more separate elements or members.

The collector of the invention is for a one-piece article consisting of three strap-connected basic components — (a) an open-mouthed base or vial, (b) a top and (c) a cap — the top being connected to the base by a first strap and the cap being connected to the top by a second strap.

The top component is either tapered or formed in the shape of a funnel in order that one end thereof shall fit the open mouth of the base whilst the opposite end thereof shall fit the hub end of a standard hypodermic needle.

The top component has a tight fit in the mouth of the base. Preferably, the top component may be "locked" in the mouth of the base by virtue of male-female interlocking snap-fit rings on their mating surfaces.

The cap has a press fit over the funnel end of the top component. When in place it yields a self-contained unit for transporting a blood sample from a collection locus to a laboratory for centrifuging and testing.

While the aforesaid unitary article may be formed of any one of a variety of resilient organic materials, e.g., plastics broadly that are inert to body fluids, it preferably is formed of high density polypropylene. This latter material is inert to body fluids; does not interfere with routine diagnostic tests; is substantially transparent; is unbreakable; can be sterilized by autoclaving; and a base or vial component made from this material has a flexion characteristic suitable for being squeezed to develop therein a subatmospheric pressure conductive to drawing a blood sample from the vein in an animal. By reason of the aforesaid locking of the top component to the base component when in use, "popping off" of the top from the base, when the device is squeezed to create suction in the act of drawing a sample, is prevented. The top component can, of course, be separated from the base, as when the sample has been centrifuged and the technician is given easy access to the plasma (or serum) overlying the deposited solids.

The three-component unitary device is relatively inexpensive to produce and hence is disposable if so desired. It is useful in collecting, transporting and testing body fluids, including blood, from animals broadly (not excluding human beings). The device is designed to conduct the bleeding of say 3.0 to 3.5 ml of blood, which amount is sufficient to perform complement fixation tests and other veterinary diagnostic tests. The base component may be, and preferably is, slightly tapered in the direction of the lower end thereof so as to accommodate the device in the centrifuge.

The invention will now be described in greater detail, and with reference to the accompanying drawings, in which FIG. 1 is a front elevational view of a preferred form of the device of the present invention, in "open" state;

Figure 1:
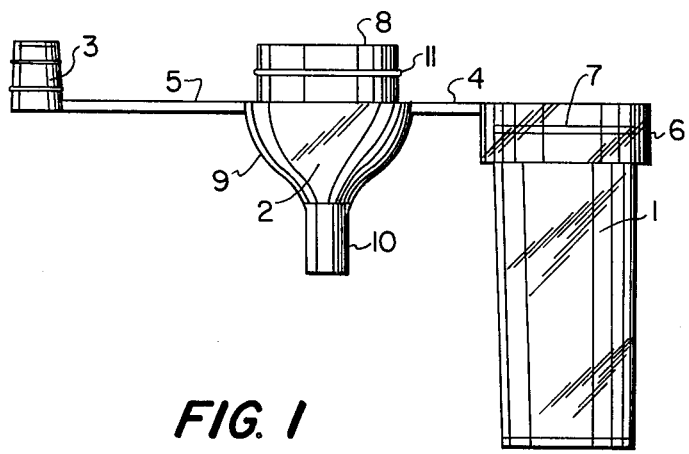
Figure 2:
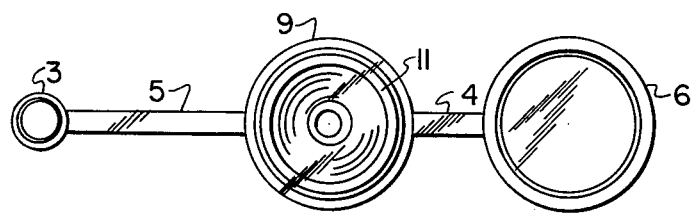
FIGS. 2 and 3 are a top plan view and a bottom plan view, respectively, of the device shown in FIG. 1.
Figure 3:
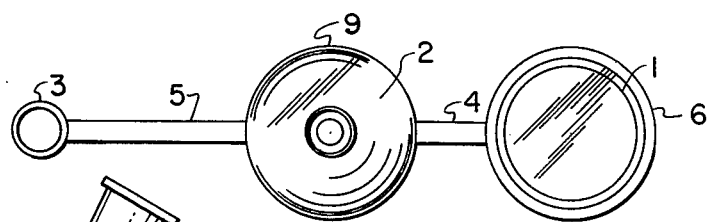

In the several figures, the one-piece device consists of a base component 1, a top component 2, a cap component 3 and connecting straps 4 and 5, respectively. When the device is in "open" state, strap 4 connects the uppermost part of base 1 to the upper part of top component 2, and strap 5 connects the upper part of top component 2 to the base of the frustoconical cap 3, said straps constituting convenient tethers, as well as flexible hinges, between the basic components. The device just described is in itself, a container for blood or other fluid. It is formed, by conventional molding technique, from high-density polypropylene. When the so-described device is associated with a conventional hypodermic needle the resulting article is a collector or bleeding device, as well as container, for blood or the like.

Base component 1 is enlarged, at its upper end, in the form of a sleeve 6 having an inner diameter substantially the same as is the outside diameter of the remainder of the base. On its inner surface sleeve 6 has an annular groove 7.

Top component 3 has the general form of a funnel, constituted by (1) a first cylindrical part 8 having an outer diameter similar to the inner diameter of sleeve 6 of base component 1, (2) an intermediate part 9 which tapers to (3) a spout-like part 10. The outer diameter of part 10 is such that said part has a tight fit in the hub of a standard hypodermic needle. An annular ridge 11 is disposed on the outer surface of cylindrical part 8 which ridge is so dimensioned and so disposed as to mate with aforesaid groove 7 when top component 2 is inserted in the mouth of base component 1.

Cap component 3 has such an inner diameter as to provide a tight fit with spout part 10 of top 2.

Figure 6:
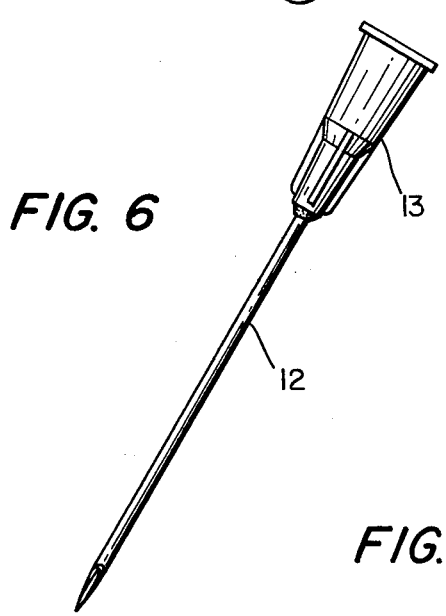
FIG. 6 is a view of a standard hypodermic needle.
Figure 4:
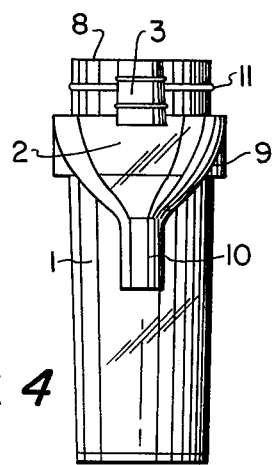
FIG. 4 is an end view of the device shown in FIG. 1 as viewed from the left.
Figure 5:
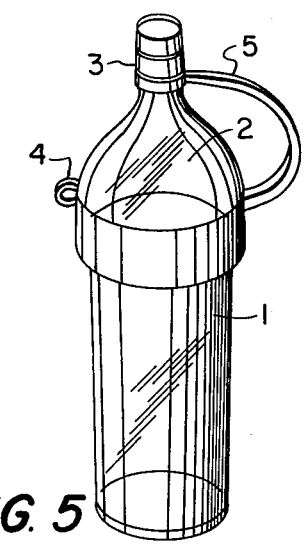
FIG. 5 is a perspective view of the device in "closed" state.

In FIG 6 there is shown a standard hypodermic needle consisting of a pointed hollow needle part 12 and a hub part 1 the inner diameter of which hub is dimensioned to yield a tight fit on the spout-like part 10 of top 2.

In using the above-described article the technician seats top part 2 securely in the sleeve 6 of base part 1, and fixes a hypodermic needle onto spout 10 of top 2; the technician squeezes base part 1 to expel some of the air present therein while inserting the needle in a vein of an animal whose blood is to be tested, and draws a small (3.0–3.5 ml) sample of blood into base 1. Then, the needle is withdrawn from the animal's vein and is separated from top part 2 of the device of the present invention. Cap component 3 is then fixed over the end of spout part 10, securely sealing the interior of the device.

The resulting sample-containing device usually is transported to a laboratory where it is set in a centrifuge and the contents subjected to centrifugal force adapted to separate the solids content of the sample to the bottom of base 1 with the liquid content of the sample (i.e., the plasma, or serum) overlying the solids. The technician removes top 2 from base component 1 and, by means of a pipette or equivalent tool, withdraws the supernatant liquid for whatever diagnostic test is desired.

While the device may be sterilized for re-use, it is customary to discard the device after a single use.

I claim:

1. A sterilizable sample container for collecting a body-fluid sample from an animal in the field and for handling the sample to perform veterinary diagnostic tests in the laboratory, having open and closed conditions and comprising a one piece, high density polypropylene molding, including a hollow generally cylindrical vial having a closed bottom end, an open top end, and one element of a groove-and-ridge combination near said open top end, said vial being collapsible upon application of a squeezing force to reduce the internal volume thereof; a first strap integral with and extending laterally from said vial at a location near said top end of said vial, said first strap being horizontal in said open condition of said container;

a top integral with that end of said first strap remote from said vial, in said open condition of said container said top having an enlarged upper end portion with the other element of said groove-and-ridge combination thereon, said upper end being of a size adapting it for cooperation with the open top end of said vial to form a snap fit between said vial and top when said top is inverted and aligned with said vial, such snap fit being secure enough to prevent said top from popping off said vial when said vial is collapsed but releasable to permit removal of said top from said vial so as to provide ready access to the contents of said vial through the entire open top end of said vial during the veterinary diagnostic tests, a smaller lower end portion, and a connecting portion joining said upper and lower end portions, said upper, lower and connecting portions having a vertical fluid passageway therethrough;

a second strap integral with and extending laterally from said top at a location spaced from said first strap, said second strap being horizontal in said open condition of said container and being located adjacent the outer circumference of the enlarged portion of the top; and a cap integral with that end of said second strap remote from said top, in the open condition of said container said cap having a closed top end, an open bottom end, and a vertical tubular wall of a size adapted to fit over the exterior surface of the smaller end portion of said top and form a press fit therewith when said top is inverted and aligned with said vial;

said first and second straps being bendable in opposite vertical directions as said container is brought from its open to its closed condition.

2. Apparatus for bleeding an animal and containing the drawn blood for transport to a testing facility comprising a one piece, high density, flexible plastic molding including a hollow, generally cylindrical base having a closed bottom end, an open top end, and one element of a groove-and-ridge combination near said open top end, said base being collapsible upon application of a squeezing force to reduce the internal volume thereof;

a first strap extending laterally from said base at a location near said top end of said base;

a top integral with that end of said first strap remote from said base said top having an enlarged first end portion with the other element of said groove-and-ridge combination thereon, said first end being of a size adapting it for cooperation with the open top end of said base to form a snap fit between said base and top, such snap fit being secure enough to prevent said top from popping off said base when said base is collapsed but releasable to permit removal of said top from said base so as to provide ready access to the contents of said base through the entire open top end of said base.

a smaller second end portion, and a connecting portion joining said first and second end portions, said first, second and connecting portions having a vertical blood passageway therethrough;

a second strap extending laterally from said top at a location spaced from said first strap; and a cap integral with that end of said second strap remote from said top said cap having a closed end, an open end, and a generally tubular wall of a size adapted to fit over the exterior surface of the smaller end portion of said top and form a press fit therewith;

said base, top and cap being permanently connected together by said straps to prevent loss and maintain the same in position for ready cooperation with one another upon flexing of said straps to permit relative movements of said base, top and cap; and a hypodermic needle unit providing a hollow needle portion and a hub part having an internal diameter adapting it for a tight fit on said smaller end portion of said top; whereby the drawn blood may be secured in said base for transport by removal of said needle unit and assembling said cap on said top; and whereby access to clotted blood components in said base may be gained by removal of said top from said base.

* * * * *